(12) United States Patent
Jaschinski et al.

(10) Patent No.: US 9,840,707 B2
(45) Date of Patent: *Dec. 12, 2017

(54) MODIFIED TGF-BETA2 OLIGONUCLEOTIDES

(71) Applicant: ISARNA Therapeutics GmbH, München (DE)

(72) Inventors: Frank Jaschinski, Obertraubling (DE); Michel Janicot, Brussels (BE); Eugen Uhlmann, Glashütten (DE)

(73) Assignee: ISARNA THERAPEUTICS GMBH, München (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/779,945

(22) PCT Filed: Mar. 27, 2014

(86) PCT No.: PCT/EP2014/056232
§ 371 (c)(1),
(2) Date: Sep. 24, 2015

(87) PCT Pub. No.: WO2014/154843
PCT Pub. Date: Oct. 2, 2014

(65) Prior Publication Data
US 2016/0060632 A1    Mar. 3, 2016

(30) Foreign Application Priority Data

Mar. 27, 2013 (EP) .................................. 13161474
Jun. 20, 2013 (EP) .................................. 13173078
Dec. 30, 2013 (EP) .................................. 13199838

(51) Int. Cl.
*C12N 15/113* (2010.01)

(52) U.S. Cl.
CPC ...... *C12N 15/1136* (2013.01); *C12N 2310/11* (2013.01); *C12N 2310/3231* (2013.01); *C12N 2310/341* (2013.01); *C12N 2310/351* (2013.01)

(58) Field of Classification Search
CPC . C12N 15/111; C12N 15/113; C12N 15/1136; A61K 31/713
See application file for complete search history.

(56) References Cited

U.S. PATENT DOCUMENTS

2011/0136893 A1* 6/2011 Schlingensiepen ........ A61K 47/48215514/44 R

FOREIGN PATENT DOCUMENTS

| EP | 1008649 A2 | 6/2000 | |
|---|---|---|---|
| EP | 2399611 A2 | 12/2011 | |
| EP | 2453017 A1 | 5/2012 | |
| WO | 1994025588 A2 | 11/1994 | |
| WO | 2004005552 A1 | 1/2004 | |
| WO | 2005084712 A2 | 9/2005 | |
| WO | WO 2005084712 A2 * | 9/2005 | ........... A61K 31/713 |
| WO | 2011154542 A1 | 12/2011 | |

OTHER PUBLICATIONS

Stanton, Robert, et al., "Chemical Modification Study of Antisense Gapmers," Nucleic Acid Therapeutics, Oct. 2012, pp. 344-359, vol. 22, No. 5.
Gordon, Kelly J., et al., "Role of transforming growth factor-beta superfamily signaling pathways in human disease," Biochimica Et Biophysica Acta, Molecular Basis of Disease, Feb. 11, 2008, pp. 197-228, vol. 1782, No. 4.
Takagi-Sato, Miho, et al., "Design of ENA® gapmers as fine-tuning antisense oligonucleotides with sequence-specific inhibitory activity on mouse PADI4 mRNA expression," Nucleic Acids Symposium Series, 2006, pp. 319-320, No. 50.
International Search Report, dated Jul. 17, 2014, and Written Opinion issued in International Application No. PCT/EP2014/056232.
Prendes, Mark A., et al., "The role of transforming growth factor beta in glaucoma and the therapeutic implications," British Journal of Ophthalmology, Jan. 15, 2013, pp. 680-686, vol. 97, No. 6.

* cited by examiner

*Primary Examiner* — J. E. Angell
(74) *Attorney, Agent, or Firm* — Gianna Julian-Arnold; Saul Ewing Arnstein & Lehr LLP

(57) ABSTRACT

The invention refers to an oligonucleotide consisting of 10 to 18 nucleotides of selected regions of the TGF-beta2 nucleic acid sequence, which comprises modified nucleotides such as LNA, ENA, polyalkylene oxide-, 2'-fluoro, 2'-O-methoxy and/or 2'-O-methyl modified nucleotides. The invention further relates to pharmaceutical compositions comprising such oligonucleotide, wherein the composition or the oligonucleotide is used in the prevention and/or treatment of a malignant and/or benign tumor, an immunologic disease, fibrosis, or an ophthalmic disease such as dry eye, glaucoma or posterior capsular opacification (PCO).

6 Claims, 10 Drawing Sheets

Fig. 1a: Nucleic acid sequence of human TGF-beta2 mRNA (SEQ ID NO. 2; NCBI Reference Sequence NM_003238.3)

```
   1 gtgatgttat ctgctggcag cagaaggttc gctccgagcg gagctccaga agctcctgac
  61 aagagaaaga cagattgaga tagagataga aagagaaaga gagaaagaga cagcagagcg
 121 agagcgcaag tgaaagaggc aggggagggg gatggagaat attagcctga cggtctaggg
 181 agtcatccag gaacaaactg aggggctgcc cggctgcaga caggaggaga cagagaggat
 241 ctattttagg gtggcaagtg cctacctacc ctaagcgagc aattccacgt tggggagaag
 301 ccagcagagg ttgggaaagg gtgggagtcc aagggagccc ctgcgcaacc ccctcaggaa
 361 taaaactccc cagccagggt gtcgcaaggg ctgccgttgt gatccgcagg gggtgaacgc
 421 aaccgcgacg gctgatcgtc tgtggctggg ttggcgtttg gagcaagaga aggaggagca
 481 ggagaaggag ggagctggag gctggaagcg tttgcaagcg gcggcggcag caacgtggag
 541 taaccaagcg ggtcagcgcg cgcccgccag ggtgtaggcc acggagcgca gctcccagag
 601 caggatccgc gccgcctcag cagcctctgc ggccctgcg gcaccgacc gagtaccgag
 661 cgccctgcga agcgcaccct cctcccgcg gtgcgctggg ctcgccccca gcgcgcgcac
 721 acgcacacac acacacacac acacacacgc acgcacacac gtgtgcgctt ctctgctccg
 781 gagctgctgc tgctcctgct ctcagcgccg cagtggaagg caggaccgaa ccgctccttc
 841 tttaaatata taaatttcag cccaggtcag cctcggcggc ccccctcacc gcgctcccgg
 901 cgccctccc gtcagttcgc cagctgccag ccccgggacc ttttcatctc ttccttttg
 961 gccgaggag ccgagttcag atccgccact ccgcacccga gactgacaca ctgaactcca
1021 cttcctcctc ttaaatttat ttctacttaa tagccactcg tctcttttt tccccatctc
1081 attgctccaa gaattttttt cttcttactc gccaaagtca gggttccctc tgcccgtccc
1141 gtattaatat ttccactttt ggaactactg gccttttctt tttaaaggaa ttcaagcagg
1201 atacgttttt ctgttgggca ttgactagat tgtttgcaaa agtttcgcat caaaaacaac
1261 aacaacaaaa aaccaaacaa ctctccttga tctatacttt gagaattgtt gatttctttt
1321 ttttattctg acttttaaaa acaacttttt tttccacttt tttaaaaaat gcactactgt
1381 gtgctgagcg cttttctgat cctgcatctg gtcacggtcg cgctcagcct gtctacctgc
1441 agcacactcg atatggacca gttcatgcgc aagaggatcg aggcgatccg cgggcagatc
1501 ctgagcaagc tgaagctcac cagtcccca gaagactatc ctgagcccga ggaagtcccc
1561 ccggaggtga tttccatcta caacagcacc agggacttgc tccaggagaa ggcgagccgg
1621 agggcggccg cctgcgagcg cgagaggagc gacgaagagt actacgccaa ggaggtttac
1681 aaaatagaca tgccgccctt cttcccctcc gaaaatgcca tccgcccac tttctacaga
1741 ccctacttca gaattgttcg atttgacgtc tcagcaatgg agaagaatgc ttccaatttg
1801 gtgaaagcag agttcagagt ctttcgtttg cagaacccaa agccagagt gcctgaacaa
1861 cggattgagc tatatcagat tctcaagtcc aaagatttaa catctccaac ccagcgctac
1921 atcgacagca aagttgtgaa aacaagagca gaaggcgaat ggctctcctt cgatgtaact
1981 gatgctgttc atgaatggct tcaccataaa gacaggaacc tgggatttaa aataagctta
2041 cactgtccct gctgcacttt tgtaccatct aataattaca tcatcccaaa taaaagtgaa
2101 gaactagaag caagatttgc aggtattgat ggcacctcca catataccag tggtgatcag
2161 aaaactataa agtccactag gaaaaaaac agtgggaaga cccacatct cctgctaatg
2221 ttattgccct cctacagact tgagtcacaa cagaccaacc ggcggaagaa gcgtgctttg
2281 gatgcggcct attgctttag aaatgtgcag gataattgct gcctacgtcc actttacatt
2341 gatttcaaga gggatctagg gtggaaatgg atacacgaac caaagggta caatgccaac
2401 ttctgtgctg gagcatgccc gtatttatgg agttcagaca ctcagcacag cagggtcctg
2461 agcttatata taccataaa tccagaagca tctgcttctc cttgctgcgt gtcccaagat
2521 ttagaaccct aaccattct ctactacatt ggcaaaacac ccaagattga acagctttct
2581 aatatgattg taaagtcttg caaatgcagc taaaattctt ggaaaagtgg caagaccaaa
2641 atgacaatga tgatgataat gatgatgacg acgacaacga tgatgcttgt aacaagaaaa
2701 cataagagag ccttggttca tcagtgttaa aaaattttg aaaaggcggt actagttcag
2761 acactttgga agtttgtgtt ctgtttgtta aaactggcat ctgacacaaa aaaagttgaa
2821 ggccttattc tacatttcac ctactttgta agtgagagag acaagaagca aatttttttt
2881 aaagaaaaaa ataaacactg aagaattta ttagtgttaa ttatgtgaac aacgacaaca
2941 acaacaacaa caacaaacag gaaaatccca ttaagtggag ttgctgtacg taccgttcct
3001 atcccgcgcc tcacttgatt tttctgtatt gctatgcaat aggcacctt cccattctta
3061 ctcttagagt taacagtgag ttatttattg tgtgttacta tataatgaac gtttcattgc
3121 ccttggaaaa taaaacaggt gtataaagtg gagaccaaat actttgccag aaactcatgg
3181 atggcttaag gaacttgaac tcaaacgagc cagaaaaaaa gaggtcatat taatgggatg
3241 aaaacccaag tgagttatta tatgaccgag aaagtctgca ttaagataaa gaccctgaaa
3301 acacatgtta tgtatcagct gcctaaggaa gcttcttgta aggtccaaaa actaaaaaga
3361 ctgttaataa aagaaacttt cagtcagaat aagtctgtaa gtttttttt tctttttaa
3421 ttgtaaatgg ttctttgtca gtttagtaaa ccagtgaaat gttgaaatgt tttgacatgt
```

Fig. 1b

```
3481 actggtcaaa cttcagacct taaaatattg ctgtatagct atgctatagg ttttttcctt
3541 tgttttggta tatgtaacca tacctatatt attaaaatag atggatatag aagccagcat
3601 aattgaaaac acatctgcag atctcttttg caaactatta aatcaaaaca ttaactactt
3661 tatgtgtaat gtgtaaattt ttaccatatt ttttatattc tgtaataatg tcaactatga
3721 tttagattga cttaaatttg ggctctttt aatgatcact cacaaatgta tgtttctttt
3781 agctggccag tacttttgag taaagcccct atagtttgac ttgcactaca aatgcatttt
3841 ttttttaata acatttgccc tacttgtgct ttgtgtttct ttcattatta tgacataagc
3901 tacctgggtc cacttgtctt ttcttttttt tgtttcacag aaaagatggg ttcgagttca
3961 gtggtcttca tcttccaagc atcattacta accaagtcag acgttaacaa attttatgt
4021 taggaaaagg aggaatgtta tagatacata gaaaattgaa gtaaatgtt ttcattttag
4081 caaggattta gggttctaac taaaactcag aatcttatt gagttaagaa aagtttctct
4141 accttggttt aatcaatatt tttgtaaaat cctattgtta ttacaaagag gacacttcat
4201 aggaaacatc ttttcttta gtcaggtttt taatattcag ggggaaattg aaagatatat
4261 attttagtcg atttttcaaa aggggaaaaa agtccaggtc agcataagtc attttgtgta
4321 tttcactgaa gttataaggt ttttataaat gttctttgaa ggggaaaagg cacaagccaa
4381 tttttcctat gatcaaaaaa ttctttcttt cctctgagtg agagttatct atatctgagg
4441 ctaaagttta ccttgcttta ataataatt tgccacatca ttgcagaaga ggtatcctca
4501 tgctggggtt aatagaatat gtcagtttat cacttgtcgc ttatttagct ttaaaataaa
4561 aattaatagg caaagcaatg gaatatttgc agtttcacct aaagagcagc ataaggaggc
4621 gggaatccaa agtgaagttg tttgatatgg tctacttctt ttttggaatt tcctgaccat
4681 taattaaaga attggatttg caagtttgaa aactggaaaa gcaagagatg ggatgccata
4741 atagtaaaca gcccttgtgt tggatgtaac ccaatcccag atttgagtgt gtgttgatta
4801 ttttttttgtc ttccactttt ctattatgtg taaatcactt ttatttctgc agacattttc
4861 ctctcagata ggatgacatt ttgttttgta ttattttgtc ttcctcatg aatgcactga
4921 taatatttta aatgctctat tttaagatct cttgaatctg ttttttttt ttttaatttg
4981 ggggttctgt aaggtcttta tttcccataa gtaaatattg ccatgggagg ggggtggagg
5041 tggcaaggaa ggggtgaagt gctagtatgc aagtgggcag caattatttt tgtgttaatc
5101 agcagtacaa tttgatcgtt ggcatggtta aaaaatggaa tataagatta gctgttttgt
5161 attttgatga ccaattacgc tgtattttaa cacgatgtat gtctgttttt gtggtgctct
5221 agtggtaaat aaattatttc gatgatatgt ggatgtcttt ttcctatcag taccatcatc
5281 gagtctagaa aacacctgtg atgcaataag actatctcaa gctggaaaag tcataccacc
5341 tttccgattg ccctctgtgc tttctccctt aaggacagtc acttcagaag tcatgcttta
5401 aagcacaaga gtcaggccat atccatcaag gatagaagaa atccctgtgc cgtcttttta
5461 ttcccttatt tattgctatt tggtaattgt ttgagattta gtttccatcc agcttgactg
5521 ccgaccagaa aaaatgcaga gagatgtttg caccatgctt tggctttctg gttctatgtt
5581 ctgccaacgc cagggccaaa agaactggtc tagacagtat cccctgtagc cccataactt
5641 ggatagttgc tgagccagcc agatataaca agagccacgt gctttctggg gttggttgtt
5701 tgggatcagc tacttgcctg tcagtttcac tggtaccact gcaccacaaa caaaaaaacc
5761 cacccctattt cctccaattt ttttggctgc tacctacaag accagactcc tcaaacgagt
5821 tgccaatctc ttaataaata ggattaataa aaaagtaat tgtgactcaa aaaaaaaaa
5881 aa
```

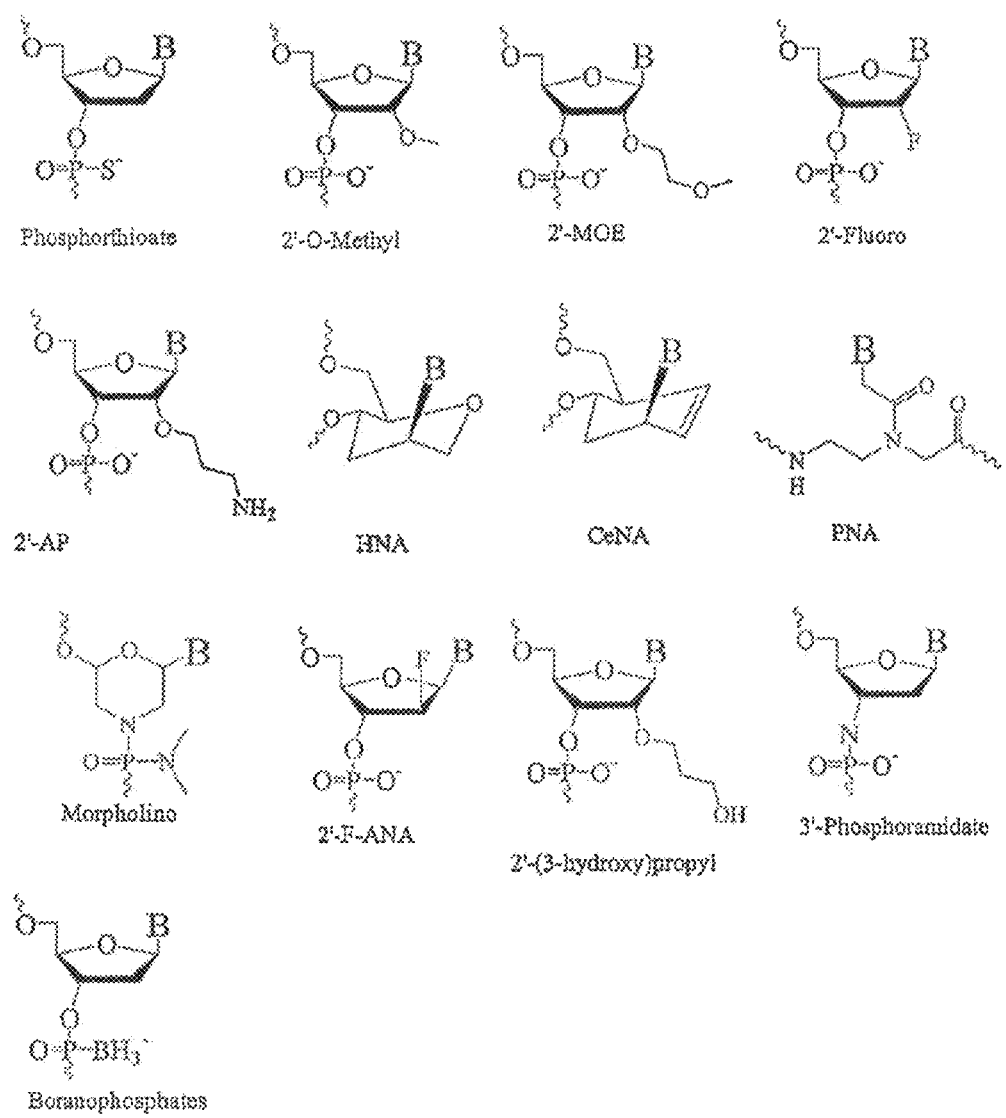
Fig. 2: Nucleotide/nucleoside modifications

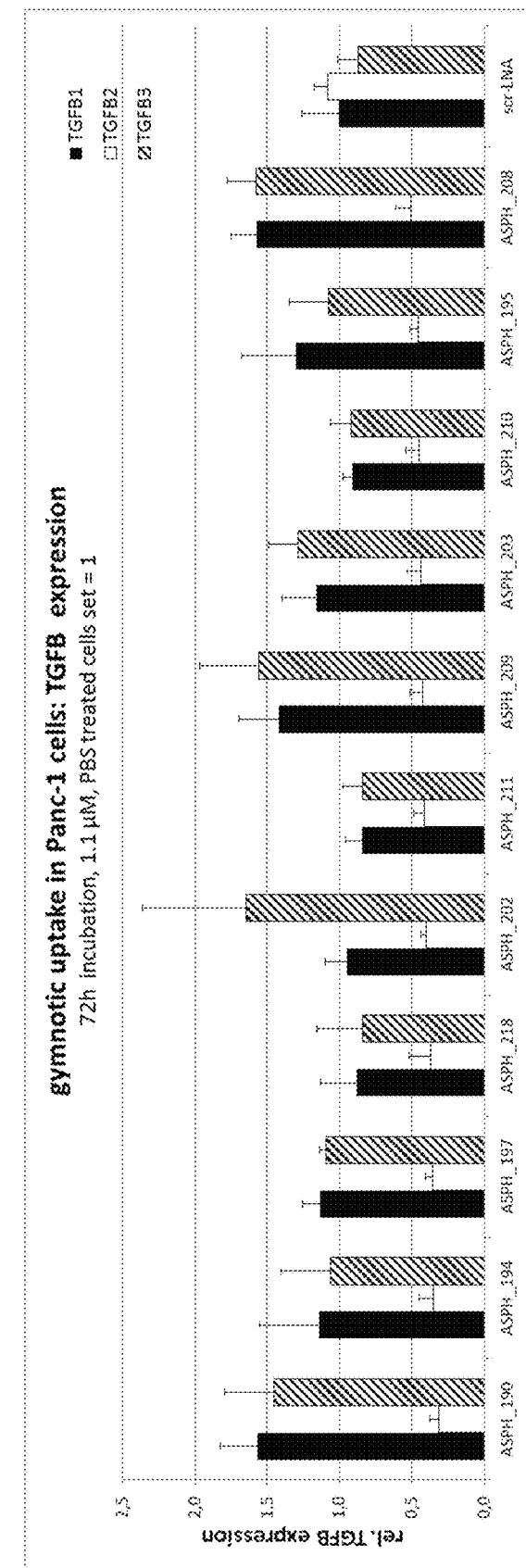
Fig. 3a(i): Inhibition of TGF-beta1, -2, or -3 expression in Panc-1 cells

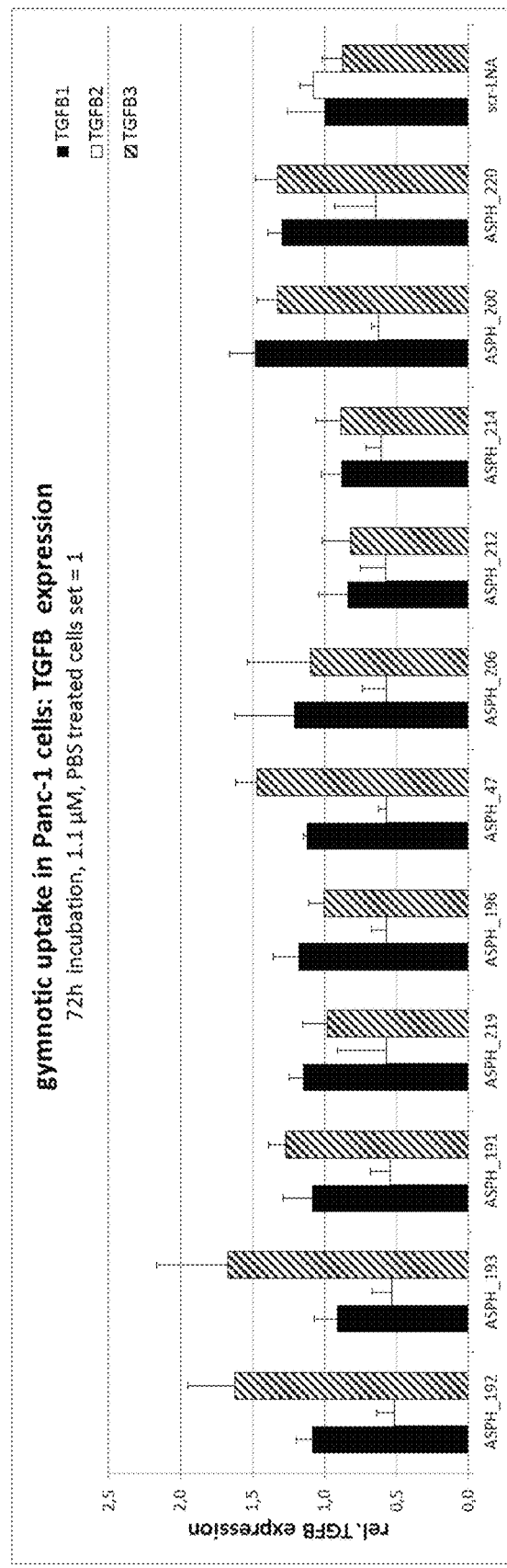
Fig. 3a(ii): Inhibition of TGF-beta1, -2, or -3 expression in Panc-1 cells

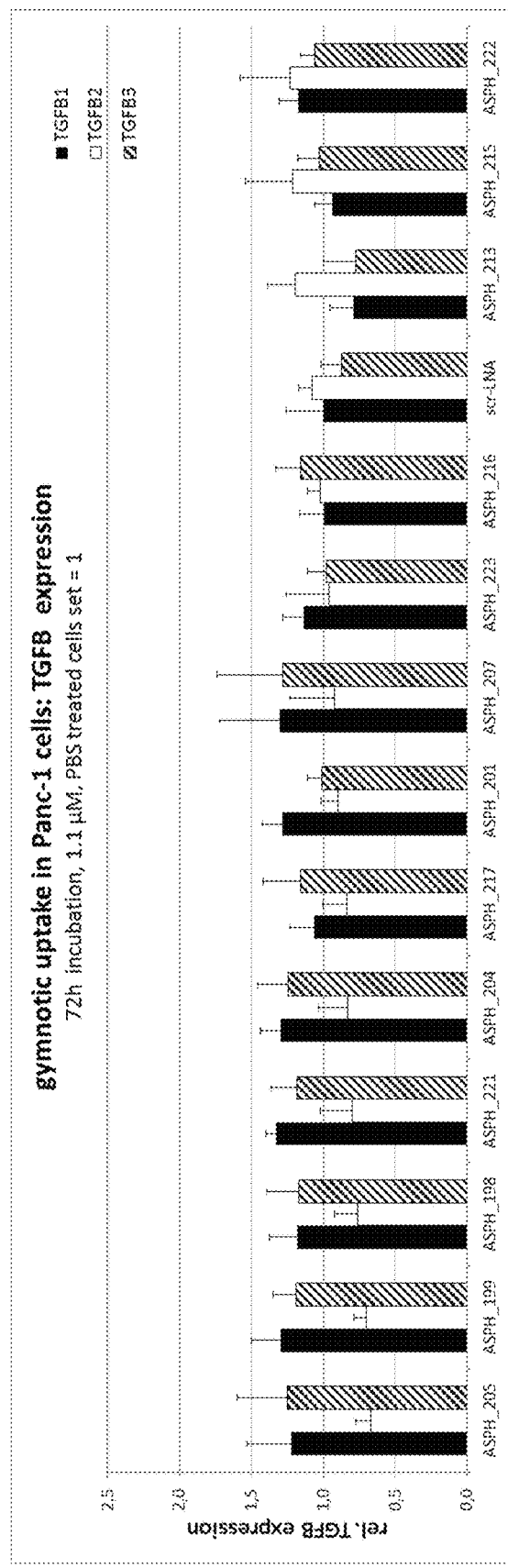
Fig. 3a(iii): Inhibition of TGF-beta1, -2, or -3 expression in Panc-1 cells

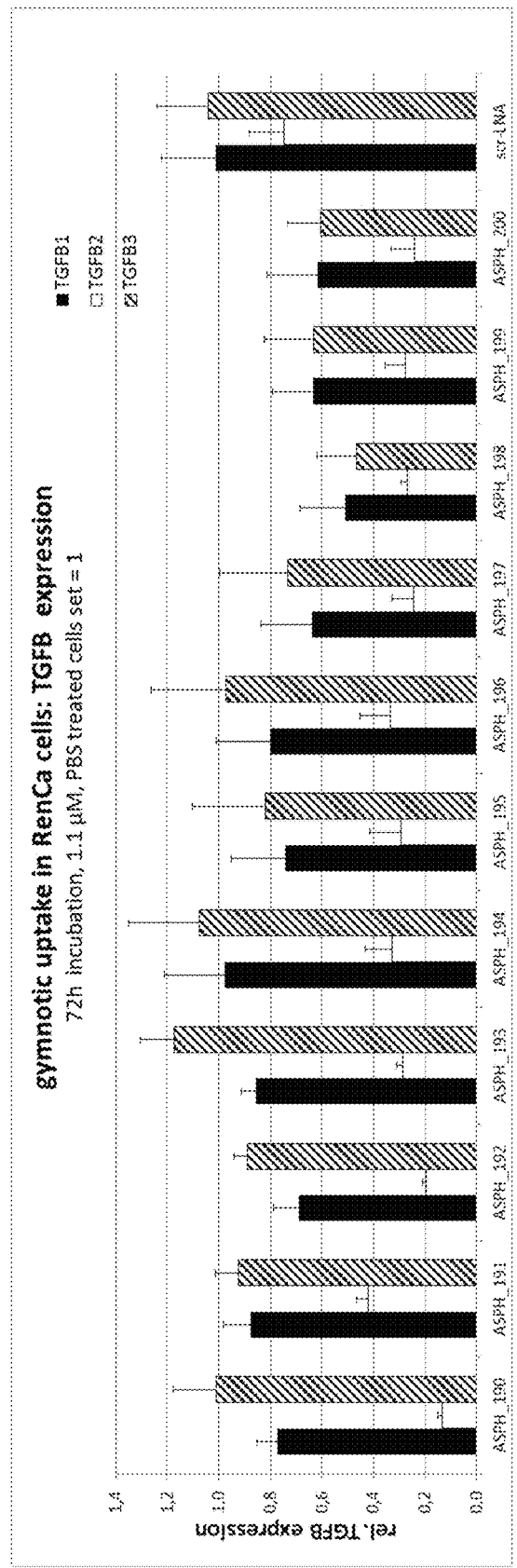
Fig. 3b(i): Inhibition of TGF-beta1, -2, or -3 expression in RenCa cells

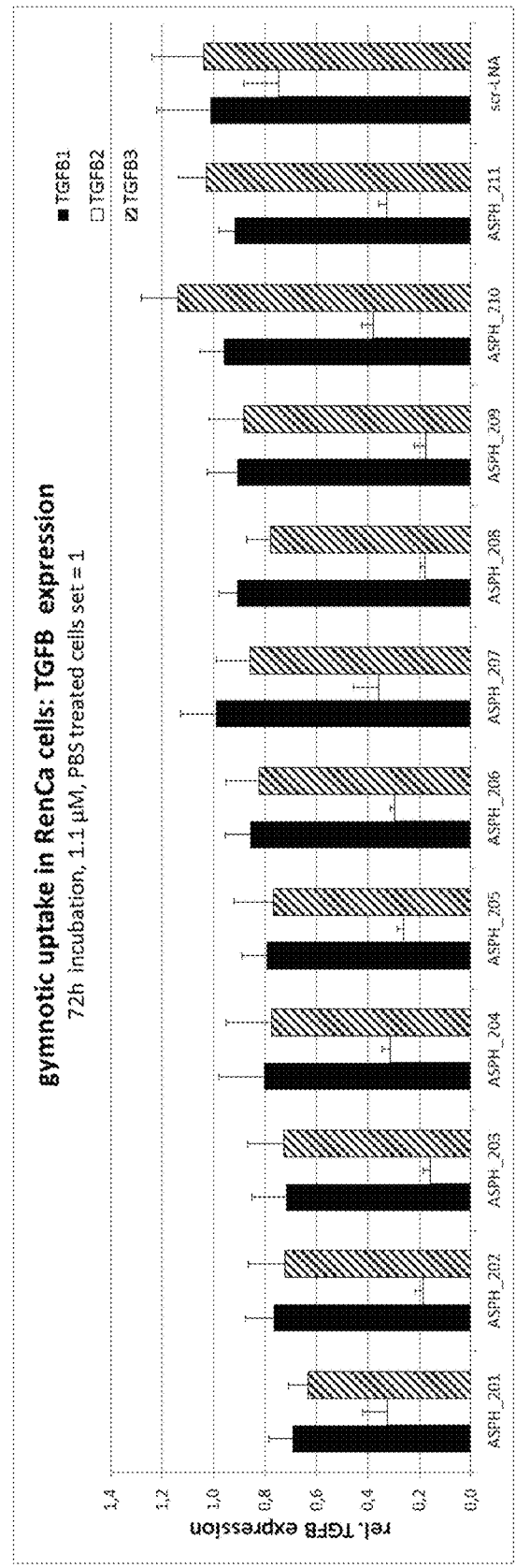
Fig. 3b(ii): Inhibition of TGF-beta1, -2, or -3 expression in RenCa cells

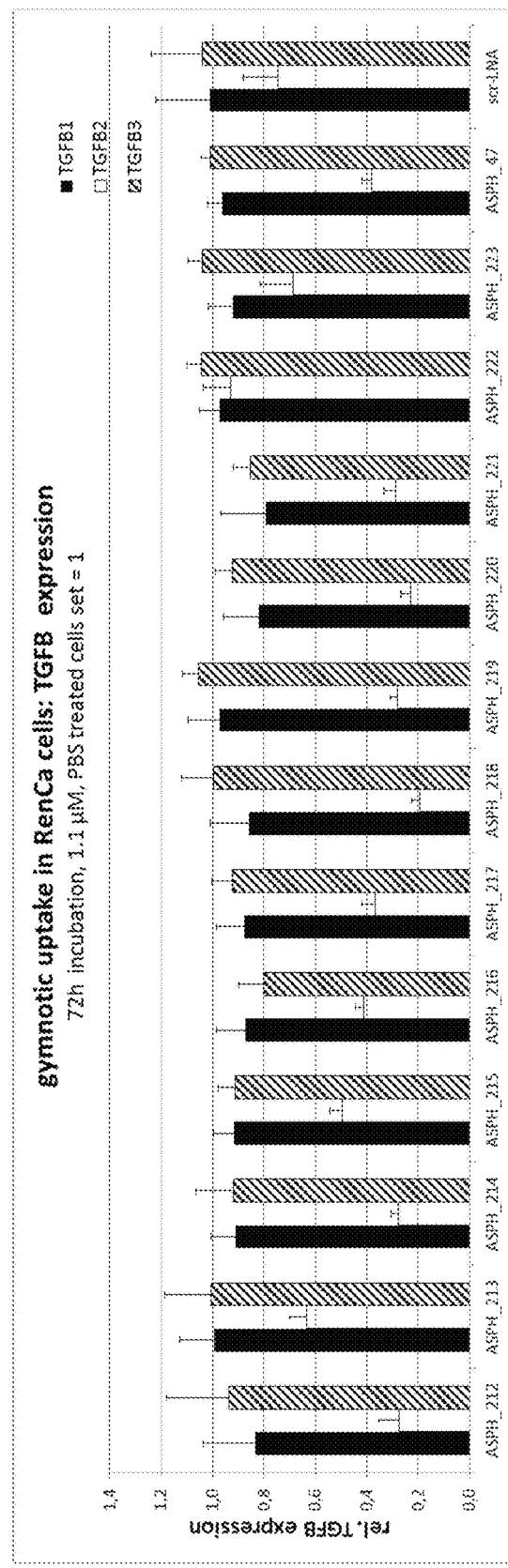
Fig. 3b(iii): Inhibition of TGF-beta1, -2, or -3 expression in RenCa cells

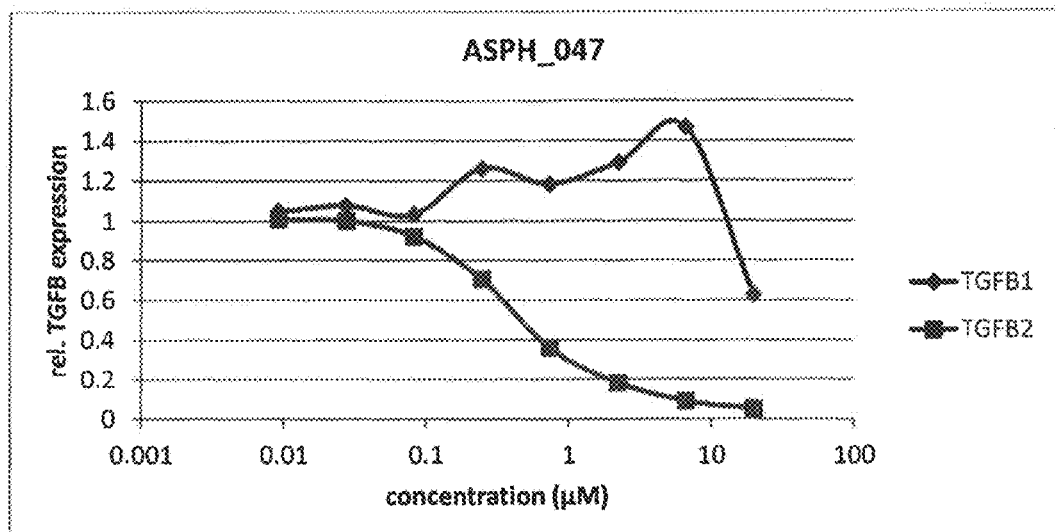
Fig. 4a: Effect on protein level by use of ASPH47
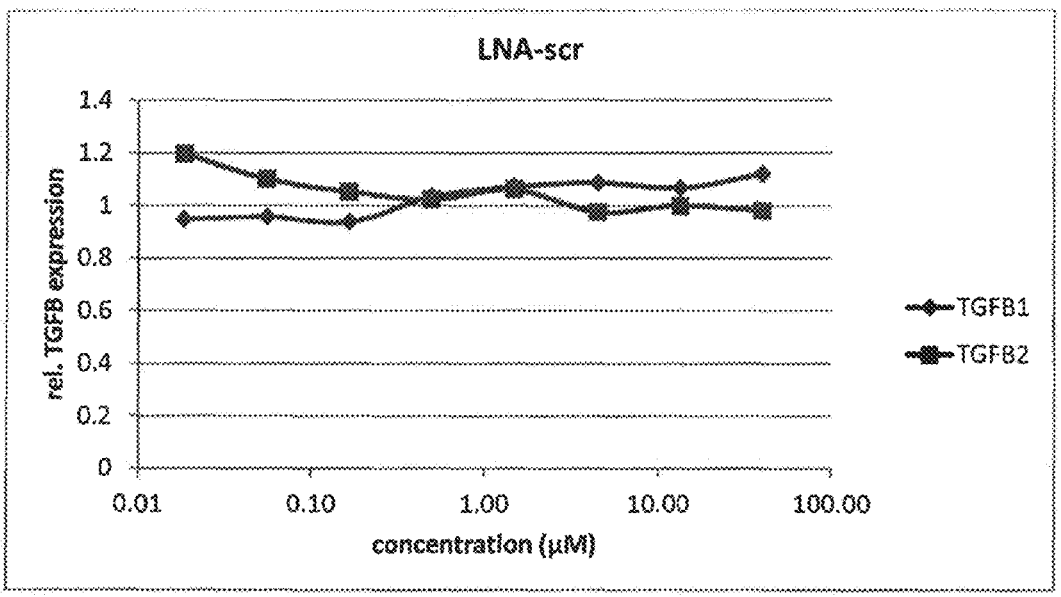
Fig. 4b: Negative control - scrLNA

MODIFIED TGF-BETA2 OLIGONUCLEOTIDES

CROSS REFERENCE TO RELATED APPLICATIONS

This application claims the priority of PCT/EP2014/056232, filed on Mar. 27, 2014, which claims priority to European Patent Application No. 13161474,5, filed on Mar. 27, 2013, European Patent Application No, 13173078.0, filed on Jun. 30, 2013, and European Patent Application No. 13199838.7, filed on Dec. 30, 2013, the entire contents of each of which are hereby incorporated in total by reference.

SEQUENCE LISTING

This application incorporates by reference the Sequence Listing contained in an ASCII text file named "362346_00027_SeqList.txt" submitted via EFS-Web. The text file was created on Sep. 24, 2015, and is 12 kb in size.

The invention is directed to oligonucleotides consisting of 10 to 18 nucleotides hybridizing with the TGF-beta2 nucleic acid sequence, the TGF-beta1 or TGF-beta3 nucleic acid sequence, wherein the oligonucleotide comprises a modified nucleotide such as LNA, ENA, polyalkylene oxide-, 2'-fluoro, 2'-O-methoxy and/or 2'-O-methyl modified nucleotides.

TECHNICAL BACKGROUND

Transforming growth factor beta (TGF-beta) is a protein that controls proliferation, cellular differentiation, and other functions in most cells. It is a type of cytokine which plays amongst others a role in immunity, cancer, heart disease, diabetes, Marfan syndrome, Loeys-Dietz syndrome, Parkinson's disease, and AIDS.

TGF-beta is a secreted protein that exists in at least three isoforms (TGF-beta-1, TGF-beta2 and TGF-beta3) encoded by different genes but sharing strong sequence and structure homologies. TGF-beta acts as an antiproliferative factor in normal epithelial cells and at early stages of oncogenesis. However, later in tumor development TGF-beta can become tumor promoting through mechanisms including the induction of epithelial-to-mesenchymal transition (EMT), a process that is thought to contribute to tumor progression, invasion and metastasis (see "Glycoproteomic analysis of two mouse mammary cell lines during transforming growth factor (TGF)-beta induced epithelial to mesenchymal transition" $7^{th}$ space.com.2009-01-08. Retrieved: 2009-01-29).

In normal (epithelial) cells, TGF-beta stops the cell cycle at the G1 stage (and stops cell proliferation), induce differentiation, or promote apoptosis. When a cell is transformed into a cancer cell, TGF-beta no longer suppresses cell proliferation, which is often the result of mutations in the signaling pathway, and cancer cells proliferate. Proliferation of stromal fibroblasts is also induced by TGF-beta. Both cells increase their production of TGF-beta. This TGF-beta acts on the surrounding stromal cells, immune cells, endothelial, smooth-muscle cells, and tumor microenvironment (see Pickupet al., "The roles of TGFβ in the tumour microenvironment", Nature Reviews Cancer (2013), 13: 788-799). Thereby, it promotes angiogenesis, and by suppressing proliferation and activation of immune cells it causes immunosuppression.

TGF-beta1-deficient mice die from cardiac, pulmonary, and gastric inflammation, suggesting that TGF-beta has a vital role in suppressing the activation and proliferation of inflammatory cells. Smad3 is one of the key elements in TGF-beta dependent downstream signling pathways. Smad3-deficient mice develop chronic mucosal infections due to impairment of T-cell activation and mucosal immunity, suggesting a key role for TGF-beta in these processes. With respect to cancer, the production and secretion of TGF-beta by certain cancer cells suppress the activities of infiltrating immune cells, thereby helping the tumor escape host immunosurveillance. This immunosuppressive effect may be another important mechanism by which TGF-beta stimulates the growth of late-stage tumors (see Blobe G C et al., May 2000, "Role of transforming growth factor beta in human disease", N. Engl. J. Med. 342 (18), 1350-1358). TGF-beta also converts effector T-cells, which normally attack cancer with an inflammatory (immune) reaction, into regulatory (suppressor) T-cells, which turn off the inflammatory reaction.

Further, TGF-beta is one of the most potent regulators of the production and deposition of extracellular matrix. It stimulates the production and affects the adhesive properties of the extracellular matrix by two major mechanisms. First, TGF-beta stimulates fibroblasts and other cells to produce extracellular-matrix proteins and cell-adhesion proteins, including collagen, fibronectin, and integrins. Second, TGF-beta decreases the production of enzymes that degrade the extracellular matrix, including collagenase, heparinase, and stromelysin, and increases the production of proteins that inhibit enzymes that degrade the extracellular matrix, including plasminogen-activator inhibitor type 1 and tissue inhibitor of metalloprotease. The net effect of these changes is to increase the production of extracellular-matrix proteins and either to increase or to decrease the adhesive properties of cells in a cell-specific manner. In many cancer cells the production of TGF-beta is increased, which increases the invasiveness of the cells by increasing their proteolytic activity and promoting their binding to cell-adhesion molecules (see Blobe GC et al., May 2000, "Role of transforming growth factor beta in human disease", N. Engl. J. Med. 342 (18), 1350-1358).

Thus, therapeutic agents which are able to influence TGF-beta expression and activity, respectively, are essential in particular for use in preventing and/or treating TGF-beta linked diseases. EP 1008649 and EP 0695354, for example, disclose oligonucleotides hybridizing with the mRNA of TGF-beta1 and/or TGF-beta2, and which are suitable to be used for manufacturing pharmaceutical compositions for example for preventing and/or treating cancer. None of these oligonucleotides comprises modifications such as LNA, ENA etc.

WO 2003/85110, WO 2005/061710, and WO 2008/138904 for example refer to oligonucleotides comprising modifications of the nucleotides, which are directed to the inhibition of HIF-1A, Bcl-2 and HER3, respectively, and usable in the treatment of cancer.

Criteria for the selection of oligonucleotides are mainly the length of the oligonucleotide, the GC-percentage, the tendency for hairpin formation, dimerization and the melting temperature (Tm). In general, high Tm (melting temperature) is preferred. Furthermore, the oligonucleotides must be specific for the target mRNA and shall not hybridize to non-target mRNAs in order to decrease potential off-target effects.

Hence, there is a high scientific and medical need for therapeutic agents, which reduce or inhibit TGF-beta expression and/or activity. Particularly, there is a long-standing need for oligonucleotides such as antisense oligonucleotides, which specifically interact and thus, reduce or inhibit the expression of TGF-beta1, TGF-beta2, and/or TGF-beta3, as well as oligonucleotides, which specifically inhibit TGF-beta1 and TGF-beta2, or TGF-beta1 and TGF-beta3, or TGF-beta2 and TGF-beta3, without causing any (severe) side effects.

SUMMARY OF THE INVENTION

The present invention refers to oligonucleotides consisting of 10 to 18 nucleotides of the TGF-beta2 nucleic acid sequence of SEQ ID NO. 1 (see FIG. 1) wherein one or more nucleotide(s) of the oligonucleotide is/are modified. Preferred oligonucleotides comprising or consisting of one of SEQ ID NO. 2 to 20 are presented in Table 1. These oligonucleotides are highly effective in the reduction and inhibition of TGF-beta2 expression and activity, respectively.

Preferred oligonucleotides of the present invention are ASPH47, ASPH190, ASPH191, ASPH192, ASPH193, ASPH194, ASPH195, ASPH196, ASPH197, ASPH198, ASPH199, ASPH200, ASPH201, and ASPH202, ASPH202, ASPH204, ASPH205, ASPH206, ASPH207, ASPH208, ASPH209, ASPH210, ASPH211, ASPH212, ASPH213, ASPH214, ASPH215, ASPH216, ASPH217, ASPH218, ASPH219, ASPH220, ASPH221, ASPH222, and ASPH223 respectivley.

Modifications of one or more nucleotides of the oligonucleotides of the present invention are selected from the group consisting of LNA, ENA, polyalkylene oxide such as triethylene glycol (TEG), 2'-fluoro, 2'-O-methoxy and 2'-O-methyl. The modifications are preferably located at the 5'- and/or 3'- end of the oligonucleotide. An oligonucleotide comprising such modified nucleotide is a modified oligonucleotide.

Modified nucleotides are for example arranged in a row, one directly next to the other, or in different patterns, where one or more unmodified nucleotides follow a modified nucleotide. For example an oligonucleotide starts with one or more modified nucleotides followed by one or more, e.g., one, two, three or four, unmodified or unlocked nucleotides followed again by one or more modified nucleotides. In one embodiment both ends of the oligonucleotide comprise an identical pattern of modified and unmodified or unlocked nucleotides. In another embodiment, the pattern of modifications at the 3'- and 5'- end differ including that one end does not comprise a modified nucleotide. Preferably the modified oligonucleotides comprise a series of 8 or 9 unlocked nucleotides.

Alternatively, a nucleotide at any other position in the oligonucleotide is modified, or at least one nucleotide at the 5'-and/or 3'-end of the oligonucleotide and at any other position in the oligonucleotide. The oligonucleotides comprise either one type of modification, or one or more different modifications. Optionally, at least one phosphate linkage between two consecutive nucleotides (modified or unmodified) of the oligonucleotide is a phosphorothioate or a methylphosphonate. In a preferred embodiment, the oligonucleotides of the present invention are phosphorothioates.

All the oligonucleotides of the different embodiments are for use in a method of the prevention and/or treatment of a malignant or a benign tumor, an immunologic disease, fibrosis (e.g., idiopathic pulmonary fibrosis, renal fibrosis, kidney fibrosis), cirrhosis (e.g., liver cirrhosis), scleroderma or related dermatologic diseases, or an eye disease such as glaucoma or posterior capsular opacification (PCO), a CNS disease, hair loss etc.

FIGURES

FIG. 1 shows the nucleic acid sequence of the the human TGF-beta2 mRNA (NM_003238.3).

FIG. 2 presents examples of nucleotide modifications.

FIG. 3 shows the inhibition of the expression of TGF-beta1, TGF-beta2 and TGF-beta3 mRNA in human Panc-1 pancreatic cancer cells and mouse RenCa renal cell carcinoma cells. Panc-1 cells and RenCa cells were treated with different modified oligonucleotides at a dose of 1.1 µM in the absence of any transfection reagent (gymnotic transfection or unassisted transfection or gymnotic delivery), and inhibition of the TGF-beta1 (black columns), TGF-beta2 (white columns), and TGF-beta3 (striped columns) mRNA expression was measured after 72 h. FIG. 3 refers to the results for the modified oligonucleotides ASPH190, ASPH191, ASPH192, ASPH193, ASPH194, ASPH195, ASPH196, ASPH197, ASPH198, ASPH199, ASPH200, ASPH201, ASPH202, ASPH203, ASPH204, ASPH205, ASPH206, ASPH207, ASPH208, ASPH209, ASPH210, ASPH211, ASPH212, ASPH213, ASPH214, ASPH215, ASPH216, ASPH217, ASPH218, ASPH219, ASPH220, ASPH221, ASPH222, and ASPH223, respectively. FIG. 3a presents the inhibitory effect of these TGF-beta oligonucleotides in Panc-1 cells and FIG. 3b in RenCa cells.

FIG. 4 depicts the inhibiting effect of oligonucleotides of the present invention on the expression of TGF-beta1 and TGF-beta2 protein. Human Panc-1 cells were transfected with 20, 6.67, 2.22, 0.74, 0.25, 0.08 or 0.009 µM of the modified oligonucleotide ASPH47 (FIG. 4a). Negative control is the scrambled oligonucleotide (scrLNA) of SEQ ID No. 22 (FIG. 4b) in concentrations of 40, 13.33, 4.44, 1.48, 0.49, 0.16, 0.05, or 0.02 µM. TGF-beta1 (diamonds) and TGF-beta2 (squares) protein levels in cell supernatants were determined by ELISA.

DETAILED DESCRIPTION

The present invention is directed to oligonucleotides, in particular antisense oligonucleotides, which comprise at least one modified nucleotide and are suitable to interact with TGF-beta mRNA, preferably with TGF-beta1, TGF-beta2, and/or TGF-beta3. The oligonucleotides comprise or consist of 10 to 18, nucleotides of the TGF-beta2 nucleic acid according to SEQ ID NO. 1. Most preferred the oligonucleotide comprises or consists of 10, 11, 12, 13, 14, 15, 16, 17, or 18 nucleotides. The oligonucleotide is a single or double stranded RNA or DNA, including siRNA, microRNA, apatmer or spiegelmer. Preferably, the oligonucleotide is an antisense oligonucleotide.

Preferred oligonucleotides of the present invention are ASPH47, ASPH190, ASPH191, ASPH192, ASPH193, ASPH194, ASPH195, ASPH196, ASPH197, ASPH198, ASPH199, ASPH200, ASPH201, and ASPH202, ASPH203, ASPH204, ASPH205, ASPH206, ASPH207, ASPH208, ASPH209,ASPH210, ASPH211, ASPH212, ASPH213, ASPH214, ASPH215, ASPH216, ASPH217, ASPH218, ASPH219, ASPH220, ASPH221, ASPH222, and ASPH223 respectivley. The antisense oligonucleotides of the present invention can be described differently, e.g., ASPH47, ASPH0047, ASPH_47 or ASPH_0047 referring to the same oligonucleotide.

A nucleotide forms the building block of an oligonucleotide, and is for example composed of a nucleobase (nitrogenous base, e.g., purine or pyrimidine), a five-carbon sugar (e.g., ribose, 2-deoxyribose, arabinose, xylose, lyxose, allose, altorse, glucose, mannose, gulose, idose, galactose, talose or stabilized modifications of those sugars), and one or more phosphate groups. Examples of modified phosphate groups are phosphorothioate or methylphosphonate. Each compound of the nucleotide is modifiable, and is naturally or non-naturally occurring. The latter are for example locked nucleic acid (LNA), a 2'-O, 4'-C-ethylene-bridged nucleic acid (ENA), polyalkylene oxide- (such as triethylene glycol (TEG)), 2'-fluoro, 2'-O-methoxy and 2'-O-methyl modified nucleotides as described for example by Freier & Altmann (Nucl. Acid Res., 1997, 25, 4429-4443) and Uhlmann (Curr. Opinion in Drug & Development (2000, 3 (2): 293-213), which are shown in FIG. 2.

A LNA is a modified RNA nucleotide, wherein the ribose moiety is modified with an extra bridge connecting the 2' oxygen and 4' carbon (2'-4'ribonucleoside). The bridge "locks" the ribose in the 3'-endo (North) conformation, which is often found in the A-form duplexes. LNA nucleosides and nucleotides, respectively, comprise for example the forms of thio-LNA, oxy-LNA, or amino-LNA, in alpha-D- or beta-L-configuration, and are mixable and combineable, respectively, with DNA or RNA residues in the oligonucleotide.

The oligonucleotides of the present invention, i.e., modified oligonucleotides, comprise at least one modified nucleotide, preferably LNA and/or ENA, at the 5'- and/or 3'-end of the oligonucleotide. In a preferred embodiment, the oligonucleotide comprises 1, 2, 3, or 4 LNAs or ENAs at the 5'-end, and 1, 2, 3, or 4 LNAs or ENAs at the 3'-end. In another preferred embodiment, the oligonucleotide comprises 1, 2, 3, or 4 LNAs or ENAs at the 5'-end or 3'-end, and a polyalkylene oxide such as TEG at the 3'- or 5'-end. The modified oligonucleotides show a significantly increased inhibition on TGF-beta expression and activity, respectively, which results in an improved prevention and/or treatment of a malignant or benign tumor, an immunologic disease, fibrosis, eye disease such as dry eye, glaucoma or posterior capsular opacification (PCO), CNS disease hair loss etc. The oligonucleotides of the present invention target TGF-beta linked diseases either by hybridization with TGF-beta mRNA, preferably TGF-beta1, TGF-beta2, or TGF-beta3.

Preferably two or more oligonucelotides are combined, wherein at least one oligonucleotide specifically inhibits TGF-beta1 and at least one oligonucleotide specifically inhibits TGF-beta2, or wherein at least one oligonucleotide specifically inhibits TGF-beta1 and at least one oligonucleotide specifically inhibits TGF-beta3, or wherein at least one oligonucleotide specifically inhibits TGF-beta2 and at least one oligonucleotide specifically inhibits TGF-beta3, or wherein at least one oligonucleotide specifically inhibits TGF-beta1, at least one oligonucleotide specifically inhibits TGF-beta2, and at least one oligonucleotide specifically inhibits TGF-beta3. The oligonucleotide of the present invention most preferably inhibits the expression and/or activity of TGF-beta2 mRNA.

In another embodiment, one oligonucleotide inhibits two TGF-beta isoforms such as TGF-beta1 and TGF-beta2, TGF-beta2 and TGF-beta3, or TGF-beta1 and TGF-beta3. An oligonucleotide inhibiting the expression of two or all three isoforms—TGF-beta1, TGF-beta2, and TGF-beta3—is defined as pan-specific oligonucleotide.

In a further embodiment three or more oligonucleotides are combined, wherein at least one oligonucleotide specifically inhibits TGF-beta1, another oligonucleotide specifically inhibits TGF-beta2, and a further oligonucleotide specifically inhibits TGF-beta3, and optionally one or more additional oligonucleotides inhibiting TGF-beta1, TGF-beta2 or TGF-beta3.

The oligonucleotides of the present invention have for example an $IC_{50}$ in the range of 0.1 to 20 µM, preferably in the range of 0.2 to 15 µM, more preferably in the range of 0.4 to 10 µM, and even more preferred in the range of 0.5 to 5 µM.

The present invention further refers to a pharmaceutical composition comprising an oligonucleotide according to the invention as active ingredient. The pharmaceutical composition comprises at least one oligonucleotide of the present invention and optionally further an antisense compound, an antibody, a chemotherapeutic compound, an anti-inflammatory compound, an antiviral compound and/or an immunomodulating compound. Pharmaceutically acceptable binding agents and adjuvants are optionally comprised by the pharmaceutical composition.

In one embodiment, the oligonucleotide and the pharmaceutical composition, respectively, is formulated as dosage unit in form of a solution comprising binders, excipients, stabilizers etc.

The oligonucleotide and/or the pharmaceutical composition is administrable via different routes. These routes of administration include, but are not limited to, electroporation, epidermal, impression into skin, intra-arterial, intra-articular, intracranial, intradermal, intra-lesional, intra-muscular, intranasal, intra-ocular, intrathecal, intracameral, intraperitoneal, intraprostatic, intrapulmonary, intraspinal, intratracheal, intratumoral, intravenous, intravesical, placement within cavities of the body, nasal inhalation, oral, pulmonary inhalation (e.g., by inhalation or insufflation of powders or aerosols, including by nebulizer), subcutaneous, subdermal, topical (including ophthalmic and to mucous membranes including vaginal and rectal delivery), or transdermal.

For parenteral, subcutaneous, intradermal or topical administration the oligonucleotide and/or the pharmaceutical composition include for example a sterile diluent, buffers, regulators of toxicity and antibacterials. In a preferred embodiment, the oligonucleotide or pharmaceutical composition is prepared with carriers that protect against degradation or immediate elimination from the body, including implants or microcapsules with controlled release properties. For intravenous administration the preferred carriers are for example physiological saline or phosphate buffered saline. An oligonucleotide and/or a pharmaceutical composition comprising such oligonucleotide for oral administration includes for example powder or granule, microparticulate, nanoparticulate, suspension or solution in water or non-aqueous media, capsule, gel capsule, sachet, tablet or minitablet. An oligonucleotide and/or a pharmaceutical composition comprising for parenteral, intrathecal, intracameral or intraventricular administration includes for example sterile aqueous solutions which optionally contain buffer, diluent and other suitable additive such as penetration enhancer, carrier compound and other pharmaceutically acceptable carrier or excipient.

A pharmaceutically acceptable carrier is for example liquid or solid, and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, a binding agent (e.g. pregelatinized maize starch, polyvinylpyrrolidone or hydroxypropyl methylcellulose, etc.); filler (e.g. lactose and other sugars, microcrystalline cellulose, pectin, gelatin, calcium sulfate, ethyl cellulose, polyacrylates or calcium hydrogen phosphate, etc.); lubricant (e.g., magnesium stearate, talcum, silica, colloidal silicon dioxide, stearic acid, metallic stearates, hydrogenated vegetable oils, corn starch, polyethylene glycols, sodium benzoate, sodium acetate, etc.); disintegrate (e.g., starch, sodium starch glycolate, etc.); or wetting agent (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404. An adjuvant is included under these phrases.

Beside being used in a method of human disease prevention and/or treatment, the oligonucleotide and/or the pharmaceutical composition according to the present invention is also used in a method for prevention and/or treatment of other subjects including veterinary animals, reptiles, birds, exotic animals and farm animals, including mammals, rodents, and the like. Mammals include for example horses, dogs, pigs, cats, or primates (for example, a monkey, a chimpanzee, or a lemur). Rodents include for example rats, rabbits, mice, squirrels, or guinea pigs.

The oligonucleotide or the pharmaceutical composition according to the invention is used in a method for the prevention and/or treatment of many different diseases, preferably benign or malignant tumors, immunologic diseases, bronchial asthma, heart disease, fibrosis (e.g., liver fibrosis, idiopathic pulmonary fibrosis, liver cirrhosis, kidney cirrhosis, scleroderma), diabetes, wound healing, disorders of the connective tissue (e.g., in heart, blood vessel, bone, joint, eye such as the Marfan or Loeys-Dietz syndrome), psoriasis, eye diseases (e.g., glaucoma, posterior capsular opacification (PCO), retinoblastoma, choroidcarcinoma, macular degeneration, such as age-related macular degeneration, diabetic macular endma, or cataract), CNS disease (e.g., Alzheimer's disease, Parkinson's disease), coronary atherosclerosis (coronary intervention or coronary artery bypass graft (CABG) surgery or hair loss. A tumor is for example selected from the group of solid tumors, blood born tumors, leukemias, tumor metastasis, hemangiomas, acoustic neuromas, neurofibromas, trachomas, pyogenic granulomas, astrocytoma such as anaplastic astrocytoma, acoustic neuroma, blastoma, Ewing's tumor, craniopharyngloma, ependymoma, medulloblastoma, glioma, glioblastoma, hemangloblastoma, Hodgkins-lymphoma, medullablastoma, leukaemia, melanoma such as primary and/or metastatic melanoma, mesothelioma, myeloma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostate cancer, small intestine carcinoma, prostate carcinoma, rectal cancer, renal cell carcinoma (RCC, e.g., clear cell RCC, papillary RCC, chromophobe RCC), oncocytoma kidney cancer, transitional cell kidney cancer, skin cancer, small-cell bronchogenic/lung carcinoma, squamous cell carcinoma, sebaceous gland carcinoma, testicular carcinoma, and uterine cancer. The oligonucleotide or the pharmaceutical composition of the present invention is not only used in a method for the prevention and/or treatment of a tumor, but likewise on a metastasis.

The present invention is preferably directed to an oligonucleotide for use in a method for prevention and/or treatment of ophthalmic diseases such as, but not limited to, retinoblastoma, choroidcarcinoma, glaucoma, posterior capsular opacification, dry eye, macular degeneration, e.g., age-related macular degeneration, diabetic macular endma, cataract, proliferative vitreoretinopathy, Marfan or Loeys-Dietz syndrome.

The antisense oligonucleotides of the present invention are characterized in that they show an unexpected low toxicity and thus, are well tolerated by different organisms. They oligonucleotides show a reasonable distribution in the organism, wherein highest concentrations are measured in the kidney, liver, skin and spleen.

The present invention provides numerous oligonucleotides, which are highly efficient in the reduction and inhibition, respectively, of TGF-beta, in particular TGF-beta2 mRNA expression due to the specific selection of the sequence of the oligonucleotide and the modification of the nucleotide. The following Table 1 shows numerous preferred modified oligonucleotides according to the present invention (modified nucleosides are indicated in bold letters). Each oligonucleotide is defined as ASPH and a number, which is defined by a specific sequence and modification of the nucleosides:

| SEQ ID NO. | Sequence | Modification | ASPH |
|---|---|---|---|
| 2 | CAAAGTATTTGGTCTCC | LNA 4 + 4 | 47 or 193 |
| 3 | AGTATTTGGTCTCC | LNA 3 + 3 | 190 or M12-ASPH47 |
| 4 | AAGTATTTGGTCTC | LNA 3 + 3 | 191 or M9-ASPH47 |
| 5 | AAGTATTTGGTCTCC | LNA 3 + 3 | 192 or M8-ASPH47 |
| 6 | AGTATTTGGTCTCC | LNA 2 + 3 | 194 |
| 6 | AGTATTTGGTCTCC | 1LNA + 1N + 1LNA + 8N + 3LNA | 195 |
| 6 | AGTATTTGGTCTCC | 3LNA + 8N + 1LNA + 1N + 1LNA | 196 |
| 6 | AGTATTTGGTCTCC | LNA 3 + 2 | 197 |
| 6 | AAGTATTTGGTCTC | LNA 4 + 2 | 198 |
| 7 | AGTATTTGGTCTCCA | 3LNA + 8N + 1LNA + 1N + 2LNA | 199 |
| 7 | AGTATTTGGTCTCCA | 3LNA + 8N + 2LNA + 1N + 1LNA | 200 |
| 7 | AGTATTTGGTCTCCA | 2LNA + 1N + 1LNA + 8N + 3LNA | 201 |
| 7 | AGTATTTGGTCTCCA | 1LNA + 1N + 2LNA + 8N + 3LNA | 202 |
| 7 | AGTATTTGGTCTCCA | LNA 3 + 2 | 203 |
| 7 | AGTATTTGGTCTCCA | LNA 2 + 3 | 204 |

| SEQ ID NO. | Sequence | Modification | ASPH |
|---|---|---|---|
| 7 | AGTATTTGGTCTCCA | LNA 2 + 4 | 205 |
| 8 | AAGTATTTGGTCTCC | 3LNA + 8N + 1LNA + 1N + 2LNA | 206 |
| 8 | AAGTATTTGGTCTCC | 3LNA + 8N + 2LNA + 1N + 1LNA | 207 |
| 8 | AAGTATTTGGTCTCC | 2LNA + 1N + 1LNA + 8N + 3LNA | 208 |
| 8 | AAGTATTTGGTCTCC | 1LNA + 1N + 2LNA + 8N + 3LNA | 209 |
| 8 | AAGTATTTGGTCTCC | LNA 3 + 2 | 210 |
| 8 | AAGTATTTGGTCTCC | LNA 2 + 3 | 211 |
| 2 | CAAAGTATTTGGTCTCC | LNA 3 + 3 | 212 |
| 2 | CAAAGTATTTGGTCTCC | LNA 2 + 2 | 213 |
| 2 | CAAAGTATTTGGTCTCC | 1LNA + 2N + 2LNA + 8N + 3LNA | 214 |
| 2 | CAAAGTATTTGGTCTCC | 1LNA + 3N + 1LNA + 8N + 3LNA | 215 |
| 2 | CAAAGTATTTGGTCTCC | 1LNA + 2N + 2LNA + 8N + 4LNA | 216 |
| 2 | CAAAGTATTTGGTCTCC | 1LNA + 2N + 2LNA + 8N + 1LNA + 1N + 2LNA | 217 |
| 2 | CAAAGTATTTGGTCTCC | 1LNA + 1N + 3LNA + 8N + 3LNA | 218 |
| 2 | CAAAGTATTTGGTCTCC | 1LNA + 1N + 2LNA + 8N + 3LNA | 219 |
| 2 | CAAAGTATTTGGTCTCC | 1LNA + 2N + 3LNA + 8N + 2LNA | 220 |
| 2 | CAAAGTATTTGGTCTCC | 1LNA + 2N + 3LNA + 8N + 1LNA + 1N + 1LNA | 221 |
| 2 | CAAAGTATTTGGTCTCC-TEG | LNA 3 + TEG | 222 |
| 2 | CAAAGTATTTGGTCTCC-TEG | LNA 4 + TEG | 223 |
| 9 | CAAAGTATTTGGTCTC | LNA 4 + 3 | M1-ASPH47 |
| 10 | CAAAGTATTTGGTCT | LNA 4 + 2 | M2-ASPH47 |
| 11 | CAAAGTATTTGGTC | LNA 4 + 1 | M3-ASPH47 |
| 12 | AAAGTATTTGGTCTC | LNA 3 + 4 | M4-ASPH47 |
| 13 | AAAGTATTTGGTCTC | LNA 3 + 3 | M5-ASPH47 |
| 14 | AAAGTATTTGGTCT | LNA 3 + 2 | M6-ASPH47 |
| 15 | AAAGTATTTGGTC | LNA 3 + 1 | M7-ASPH47 |
| 16 | AAGTATTTGGTCT | LNA 2 + 2 | M10-ASPH47 |
| 17 | AAGTATTTGGTC | LNA 2 + 1 | M11-ASPH47 |
| 18 | AGTATTTGGTCTC | LNA 1 + 3 | M13-ASPH47 |
| 19 | AGTATTTGGTCT | LNA 1 + 2 | M14-ASPH47 |
| 20 | AGTATTTGGTC | LNA 1 + 1 | M15-ASPH47 |

Table 1 shows the nucleic acid sequences of selected oligonucleotides of the present invention as well as the modifications of the nucleotides, wherein LNA 4+4 means 4×LNAs at the 5'- and 3'-end of the oligonucleotide are modified, wherein LNA 4+3 means 4×LNAs at the 5'-end and 3×LNAs at the 3'-end of the oligonucleotide are modified, wherein LNA 3+4 means 3×LNAs at the 5'-end and 4×LNAs at the 3'-end of the oligonucleotide are modified, wherein LNA 3+3 means 3×LNAs at the 5'- and 3'-end of the oligonucleotide are modified, wherein LNA 3+2 means 3×LNAs at the 5'-end and 2×LNAs at the 3'-end of the oligonucleotide are modified, wherein LNA 2+3 means 2×LNAs at the 5'-end and 3×LNAs at the 3'-end of the oligonucleotide are modified, wherein LNA 2+2 means 2×LNAs at the 5'- and 3'-end of the oligonucleotide are modified. Alternatively, some oligonucleotides comprise ENA 4+4, i.e., 4×ENA at the 5'- and 3'- end of the oligonucleotide are modified, or ENA 3+3, i.e., 3×ENA at the 5'- and 3'- end of the oligonucleotide are modified. Further oligonucleotides comprise 2'O-meth 4+4, wherein the oligonucleotide comprises 4×2'O-methyl modified nucleotides at the 5'- and 3'-end of the oligonucleotide, or comprises 2' fluoro 4+4, wherein the oligonucleotide comprises 4×2' fluoro modified nucleotides at the 5'-end and 3'-end. Oligonucleotides comprising LNA 3+TEG comprise 3×LNAs at the 5'-end and one triethylene glycol (TEG) at the 3'-end of the oligonucleotide. Some oligonucleotides comprise LNAs which are not arranged in a row but are separated by an unlocked (unmodified) nucleoside having for example the sequences 1LNA+1N+1LNA+8N+3LNA, 3LNA+8N+1LNA+1N+1LNA, 3LNA+8N+1LNA+1N+2LNA, 3LNA+8N+2LNA+1N+1LNA, 2LNA+1N+1LNA+8N+3LNA, 1LNA+1N+2LNA+8N+3LNA, 1LNA+2N+2LNA+8N+3LNA, 1LNA+3N+1LNA+8N+3LNA, 1LNA+2N+2LNA+8N+4LNA, 1LNA+2N+2LNA+8N+1LNA+1N+2LNA, 1LNA+1N+3LNA+8N+3LNA, 1LNA+1N+2LNA+8N+3LNA, 1LNA+2N+3LNA+8N+2LNA, or 1LNA+2N+3LNA+8N+1LNA+1N+1LNA, wherein "N" is a nucleoside without locked modification. LNA nucleosides are indicated in the sequence in bold letters, and triethylene glycol is abbreviated as TEG in this table. "ASPH" in combination with a number refers to the different oligonucleotides and their different modifications as described in Table 1. The antisense oligonucleotides of the present invention can be described differently, e.g., ASPH47, ASPH0047, ASPH_47 or ASPH_0047 referring to the same oligonucleotide. These modified oligonucleotides were tested e.g. in experiments shown in the following examples.

For the purpose of clarity and a concise description, features are described herein as part of the same or separate embodiments, however, it will be appreciated that the scope of the invention may include embodiments having combinations of all or some of the features described.

The following examples will serve to further illustrate the present invention without, at the same time, however, constituting any limitation thereof. On the contrary, it is to be clearly understood that the scope of the present invention refers to various other embodiments, modifications, and equivalents thereof which, after reading the description herein, may suggest themselves to those skilled in the art without departing from the spirit of the invention.

EXAMPLES

In the following examples, the effect of the oligonucleotides listed in Table 1 has been tested in view of the reduction and inhibition, respectively, of TGF-beta1 and/or TGF-beta2 expression. SEQ ID NO. 21 (T-LNA: CGGCATGTCTATTTTGTA, wherein 3×nucleotides at the 5'- and 3'-end are LNAs) and SEQ ID NO. 22 (scr-LNA: CGTTTAGGCTATGTACTT, wherein 3×nucleotides at the 5'- and 3'-end are LNAs) are used as control oligonucleotides, wherein SEQ ID NO. 22 (negative control) is the scrambled form of SEQ ID NO. 21 (positive control). The cells were either transfected in the presence of a transfecting agent (e.g., Lipofectamine), or in the absence of any transfecting agent (which is defined as gymnotic transfection or unassisted transfection or gymnotic delivery). In case of gymnotic delivery, the entry of the oligonucleotide into the cell solely depends on the interaction of the oligonucleotide with the cell (no agent supports the entry). Therefore, gymnotic delivery is considered to reflect better conditions of the in vivo settings.

Example 1

Either human Panc-1 pancreatic cancer cells (FIG. 3a) or mouse RenCa renal cell carcinoma cells (FIG. 3b) were treated with 1.1 μM of ASPH190, ASPH191, ASPH192, ASPH 193, ASPH 194, ASPH 195, ASPH 196, ASPH 197, ASPH 198, ASPH 199, ASPH200, ASPH201, ASPH202, ASPH203, ASPH204, ASPH205, ASPH206, ASPH207, ASPH208, ASPH209, ASPH210, ASPH211, ASPH212, ASPH213, ASPH214, ASPH215, ASPH216, ASPH217, ASPH218, ASPH219, ASPH220, ASPH221, ASPH222, or ASPH223 in the absence of a transfecting agent (gymnotic transfection or gymnotic delivery). The expression of TGF-beta1 (black column), TGF-beta2 (white column) and TGF-beta3 (striped column) mRNA was determined 72 h after transfection. Significant reduction of the expression of TGF-beta2 mRNA is demonstrated in FIGS. 3a and 3b. The negative control is scrambled LNA (scr LNA) of SEQ ID No. 22.

Example 2

Human Panc-1 pancreatic cancer cells were treated with 10 μM, 3.3 μM, 1.1 μM, 0.37 μM, and 0.12 μM of ASPH47, M1-ASPH47, M2-ASPH47, M3-ASPH47, M4-ASPH47, M5-ASPH47, M6-ASPH47, M7-ASPH47, M8-ASPH47, M9-ASPH47, M10-ASPH47, M11-ASPH47, M12-ASPH47, M13-ASPH47, M14-ASPH47, or M15-ASPH47 in the absence of a transfecting agent (gymnotic transfection or gymnotic delivery). The inhibitory effect of the modified oligonucleotides on expression of TGF-beta2 mRNA was determined 72 h after treatment start. TGF-beta2 values were normalized to GAPDH and oligonucleotide concentrations resulting in 50% reduction of TGF-beta2 mRNA (=$IC_{50}$ values) were calculated. Under gymnotic transfection experimental conditions, the oligonucleotides enter the cells and strongly inhibit the expression of TGF-beta2 mRNA. The results of the experiments are shown in Table 2:

| oligos | $IC_{50}$ (μM) |
| --- | --- |
| M1__ASPH__0047 | 0.3 |
| M2__ASPH__0047 | 0.49 |
| M3__ASPH__0047 | 1.75 |
| M4__ASPH__0047 | 0.95 |
| M5__ASPH__0047 | 0.85 |
| M6__ASPH__0047 | 1.49 |
| M7__ASPH__0047 | n.a. |
| M8__ASPH__0047 | 0.89 |
| M9__ASPH__0047 | 1.05 |
| M10__ASPH__0047 | 7.75 |
| M11__ASPH__0047 | n.a. |
| M12__ASPH__0047 | 1.58 |
| M13__ASPH__0047 | 1.91 |
| M14__ASPH__0047 | n.a. |
| M15__ASPH__0047 | n.a. |
| ASPH__0047 | 0.348 |

All the modified oligonucleotides show an $IC_{50}$ in the submicromolar to lower submicromolar range, showing that they have extremely high potency even without the requirement of a transfection reagent.

Example 3

Human Panc-1 pancreatic cancer cells were transfected with 20, 6.67, 2.22, 0.74, 0.25, 0.08 or 0.009 μM of the modified oligonucleotide ASPH47, and results are shown in FIG. 4a. Negative control is the scrambled oligonucleotide (scr LNA) of SEQ ID No. 22 (FIG. 4b). Cells were transfected in the absence of a transfecting agent (gymnotic transfection or gymnotic delivery). The oligonucleotides were added to the cells for 3 days, which were incubated at 37° C. Thereafter medium was exchanged with fresh oligonucleotide containing medium and cells were incubated for further 4 days at 37° C. TGF-beta1 and TGF-beta2 protein levels in cell supernatants were determined by ELISA. ASPH47 specifically inhibits the expression of TGF-beta2 in a dose-dependent manner and does not show target inhibiting effect on TGF-beta1 (FIG. 4a). The scrLNA of SQE ID No. 22 does not show any inhibiting effect on the expression of TGF-beta1 or TGF-beta2, even if the concentrations were doubled (40, 13.33, 4.44, 1.48, 0.49, 0.16, 0.05, or 0.02 μM) in comparison to the individual concentrations of ASPH47. Results for TGF-beta1 are indicated in diamonds, and results for TGF-beta2 in squares in FIGS. 4a and 4b.

What is claimed is:

1. A method of inhibiting and/or treating a malignant and/or benign tumor, an immunologic disease, fibrosis, or an ophthalmic disease comprising: administering a pharmaceutical composition to a subject in need thereof, said pharmaceutical composition comprising:
   an antisense oligonucleotide, wherein said antisense oligonucleotide comprises a sequence selected from the group consisting of SEQ ID NO. 2, SEQ ID NO. 3, SEQ ID NO. 4, SEQ ID NO. 5, SEQ ID NO. 6, SEQ ID NO. 7, SEQ ID NO. 8, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16, SEQ ID NO.17, and SEQ ID NO. 18 wherein said antisense oligonucleotide is 10 to 18 nucleotides in length and wherein one or more nucleotide(s) of the oligonucleotide is/are modified.

2. A method of inhibiting and/or treating a malignant and/or benign tumor, an immunologic disease, fibrosis, or an ophthalmic disease comprising: administering a pharmaceutical composition to a subject in need thereof, said pharmaceutical composition comprising:
   an antisense oligonucleotide, wherein said antisense oligonucleotide is selected from the group consisting of AGTATTTGGTCTCC (SEQ ID NO. 3), AAGTATTTGGTCTC (SEQ ID NO. 4), AAGTATTTGGTCTCC (SEQ ID NO. 5), CAAAGTATTTGGTCTCC (SEQ ID NO. 2), AGTATTTGGTCTCC (SEQ ID NO. 6), AGTATTTGGTCTCC (SEQ ID NO. 6), AGTATTTGGTCTCC (SEQ ID NO. 6), AGTATTTGGTCTCC (SEQ ID NO. 6), AAGTATTTGGTCTC (SEQ ID NO. 6), AGTATTTGGTCTCCA (SEQ ID NO. 7), AGTATTTGGTCTCCA (SEQ ID NO. 7), AGTATTTGGTCTCCA (SEQ ID NO. 7), AGTATTTGGTCTCCA (SEQ ID NO. 7), AGTATTTGGTCTCCA (SEQ ID NO. 7), AGTATTTGGTCTCCA (SEQ ID NO. 7), AAGTATTTGGTCTCC (SEQ ID NO. 8), AAGTATTTGGTCTCC (SEQ ID NO. 8), AAGTATTTGGTCTCC (SEQ ID NO. 8), AAGTATTTGGTCTCC (SEQ ID NO. 8), AAGTATTTGGTCTCC (SEQ ID NO. 8), AAGTATTTGGTCTCC (SEQ ID NO. 8), CAAAGTATTTGGTCTCC (SEQ ID NO. 2), CAAAGTATTTGGTCTCC (SEQ ID NO. 2), CAAAGTATTTGGTCTCC (SEQ ID NO. 2), CAAAGTATTTGGTCTCC (SEQ ID NO. 2), CAAAGTATTTGGTCTCC (SEQ ID NO. 2), CAAAGTATTTGGTCTCC (SEQ ID NO. 2), CAAAGTATTTGGTCTCC (SEQ ID NO. 2), CAAAGTATTTGGTCTCC (SEQ ID NO. 2), CAAAGTATTTGGTCTCC (SEQ ID NO. 2), CAAAGTATTTGGTCTCC (SEQ ID NO. 2), CAAAGTATTTGGTCTCC-TEG (SEQ ID NO. 2), CAAAGTATTTGGTCTCC-TEG (SEQ ID NO. 2), CAAAGTATTTGGTCTC (SEQ ID NO. 9), CAAAGTATTTGGTCT (SEQ ID NO. 10), CAAAGTATTTGGTC (SEQ ID NO. 11), AAAGTATTTGGTCTCC (SEQ ID NO. 12), AAAGTATTTGGTCTC (SEQ ID NO. 13), AAAGTATTTGGTCT (SEQ ID NO. 14), AAAGTATTTGGTC (SEQ ID NO. 15), AAGTATTTGGTCTCC (SEQ ID NO. 5), AAGTATTTGGTCTC (SEQ ID NO. 4), AAGTATTTGGTCT (SEQ ID NO. 16), AAGTATTTGGTC (SEQ ID NO. 17), AGTATTTGGTCTCC (SEQ ID NO. 3), AGTATTTGGTCTC (SEQ ID NO. 18), AGTATTTGGTCT (SEQ ID NO. 19), and AGTATTTGGTC (SEQ ID NO. 20); wherein the nucleotides in bold are LNA-modified nucleotides.

3. The method of claim 1, wherein the method is directed to inhibiting and/or treating a malignant and/or benign tumor, and wherein the tumor is at least one of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngioma, ependymoma, medulloblastoma, glioma, hemangloblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostata cancer, small intestine carcinoma, prostate carcinoma, rectal cancer, renal cell carcinoma, skin cancer, small-cell bronchogenic/lung carcinoma, squamous cell carcinoma, sebaceous gland carcinoma, testicular carcinoma, or uterine cancer.

4. The method of claim 1 wherein the method is directed to inhibiting and/or treating ophthalmic disease and wherein the ophthalmic disease is selected from the group consisting of glaucoma, posterior capsular opacification, dry eye, macular degeneration, age-related macular degeneration, diabetic macular endma, cataract, proliferative vitreoretinopathy, Marfan and Loeys-Dietz syndrome.

5. The method of claim 2, wherein the method is directed to inhibiting and/or treating ophthalmic disease and wherein the ophthalmic disease is selected from the group consisting of glaucoma, posterior capsular opacification, dry eye, macular degeneration, age-related macular degeneration, diabetic macular endma, cataract, proliferative vitreoretinopathy, Marfan and Loeys-Dietz syndrome.

6. The method of claim 2, wherein the method is directed to inhibiting and/or treating a malignant and/or benign tumor, and wherein the tumor is at least one of solid tumors, blood born tumors, leukemias, tumor metastasis, hemangiomas, acoustic neuromas, neurofibromas, trachomas, pyogenic granulomas, psoriasis, astrocytoma, acoustic neuroma, blastoma, Ewing's tumor, craniopharyngioma, ependymoma, medulloblastoma, glioma, hemangloblastoma, Hodgkins-lymphoma, medullablastoma, leukaemia, mesothelioma, neuroblastoma, neurofibroma, non-Hodgkins lymphoma, pinealoma, retinoblastoma, sarcoma, seminoma, trachomas, Wilm's tumor, bile duct carcinoma, bladder carcinoma, brain tumor, breast cancer, bronchogenic carcinoma, carcinoma of the kidney, cervical cancer, choriocarcinoma, cystadenocarcinome, embryonal carcinoma, epithelial carcinoma, esophageal cancer, cervical carcinoma, colon carcinoma, colorectal carcinoma, endometrial cancer, gallbladder cancer, gastric cancer, head cancer, liver carcinoma, lung carcinoma, medullary carcinoma, neck cancer, non-small-cell bronchogenic/lung carcinoma, ovarian cancer, pancreas carcinoma, papillary carcinoma, papillary adenocarcinoma, prostata cancer, small intestine carcinoma, prostate carcinoma, rectal cancer, renal cell carcinoma, skin cancer, small-cell bronchogenic/lung carcinoma, squamous cell carcinoma, sebaceous gland carcinoma, testicular carcinoma, or uterine cancer.

\* \* \* \* \*

SEQUENCE LISTING

<160> NUMBER OF SEQ ID NOS: 20

<210> SEQ ID NO 1
<211> LENGTH: 5882
<212> TYPE: DNA

<213> ORGANISM: Homo sapiens

<400> SEQUENCE: 1

| | | | | | |
|---|---|---|---|---|---|
| gtgatgttat | ctgctggcag | cagaaggttc | gctccgagcg | gagctccaga | agctcctgac | 60 |
| aagagaaaga | cagattgaga | tagagataga | aagagaaaga | gagaaagaga | cagcagagcg | 120 |
| agagcgcaag | tgaaagaggc | aggggagggg | gatggagaat | attagcctga | cggtctaggg | 180 |
| agtcatccag | gaacaaactg | aggggctgcc | cggctgcaga | caggaggaga | cagagaggat | 240 |
| ctattttagg | gtggcaagtg | cctacctacc | ctaagcgagc | aattccacgt | tggggagaag | 300 |
| ccagcagagg | ttgggaaagg | gtgggagtcc | aagggagccc | ctgcgcaacc | ccctcaggaa | 360 |
| taaaactccc | cagccagggt | gtcgcaaggg | ctgccgttgt | gatccgcagg | gggtgaacgc | 420 |
| aaccgcgacg | gctgatcgtc | tgtggctggg | ttggcgtttg | gagcaagaga | aggaggagca | 480 |
| ggagaaggag | ggagctggag | gctggaagcg | tttgcaagcg | gcggcggcag | caacgtggag | 540 |
| taaccaagcg | ggtcagcgcg | cgcccgccag | ggtgtaggcc | acggagcgca | gctcccagag | 600 |
| caggatccgc | gccgcctcag | cagcctctgc | ggccctgcg | gcaccgacc | gagtaccgag | 660 |
| cgccctgcga | agcgcaccct | cctccccgcg | gtgcgctggg | ctcgccccca | gcgcgcgcac | 720 |
| acgcacacac | acacacacac | acacacacgc | acgcacacac | gtgtgcgctt | ctctgctccg | 780 |
| gagctgctgc | tgctcctgct | ctcagcgccg | cagtggaagg | caggaccgaa | ccgctccttc | 840 |
| tttaaatata | taaatttcag | cccaggtcag | cctcggcggc | ccccctcacc | gcgctcccgg | 900 |
| cgcccctccc | gtcagttcgc | cagctgccag | ccccgggacc | ttttcatctc | ttcccttttg | 960 |
| gccggaggag | ccgagttcag | atccgccact | ccgcacccga | gactgacaca | ctgaactcca | 1020 |
| cttcctcctc | ttaaatttat | ttctacttaa | tagccactcg | tctcttttt | tccccatctc | 1080 |
| attgctccaa | gaatttttt | cttcttactc | gccaaagtca | gggttccctc | tgcccgtccc | 1140 |
| gtattaatat | ttccactttt | ggaactactg | gccttttctt | tttaaaggaa | ttcaagcagg | 1200 |
| atacgtttt | ctgttgggca | ttgactagat | tgtttgcaaa | agtttcgcat | caaaaacaac | 1260 |
| aacaacaaaa | aaccaaacaa | ctctccttga | tctatacttt | gagaattgtt | gatttcttt | 1320 |
| ttttattctg | acttttaaaa | acaacttttt | tttccacttt | tttaaaaaat | gcactactgt | 1380 |
| gtgctgagcg | cttttctgat | cctgcatctg | gtcacggtcg | cgctcagcct | gtctacctgc | 1440 |
| agcacactcg | atatggacca | gttcatgcgc | aagaggatcg | aggcgatccg | cgggcagatc | 1500 |
| ctgagcaagc | tgaagctcac | cagtcccca | gaagactatc | ctgagcccga | ggaagtcccc | 1560 |
| ccggaggtga | tttccatcta | caacagcacc | agggacttgc | tccaggagaa | ggcgagccgg | 1620 |
| agggcggccg | cctgcgagcg | cgagaggagc | gacgaagagt | actacgccaa | ggaggtttac | 1680 |
| aaaatagaca | tgccgccctt | cttccccctcc | gaaaatgcca | tcccgcccac | tttctacaga | 1740 |
| ccctacttca | gaattgttcg | atttgacgtc | tcagcaatgg | agaagaatgc | ttccaatttg | 1800 |
| gtgaaagcag | agttcagagt | ctttcgtttg | cagaacccaa | aagccagagt | gcctgaacaa | 1860 |
| cggattgagc | tatatcagat | tctcaagtcc | aaagatttaa | catctccaac | ccagcgctac | 1920 |
| atcgacagca | agttgtgaa | aacaagagca | gaaggcgaat | ggctctcctt | cgatgtaact | 1980 |
| gatgctgttc | atgaatggct | tcaccataaa | gacaggaacc | tgggatttaa | aataagctta | 2040 |
| cactgtccct | gctgcacttt | tgtaccatct | aataattaca | tcatcccaaa | taaaagtgaa | 2100 |
| gaactagaag | caagatttgc | aggtattgat | ggcacctcca | catataccag | tggtgatcag | 2160 |
| aaaactataa | agtccactag | gaaaaaaac | agtgggaaga | cccacatctc | cctgctaatg | 2220 |
| ttattgccct | cctacagact | tgagtcacaa | cagaccaacc | ggcggaagaa | gcgtgctttg | 2280 |

```
gatgcggcct attgctttag aaatgtgcag gataattgct gcctacgtcc actttacatt    2340
gatttcaaga gggatctagg gtggaaatgg atacacgaac ccaaagggta caatgccaac    2400
ttctgtgctg gagcatgccc gtatttatgg agttcagaca ctcagcacag cagggtcctg    2460
agcttatata ataccataaa tccagaagca tctgcttctc cttgctgcgt gtcccaagat    2520
ttagaacctc taaccattct ctactacatt ggcaaaacac ccaagattga acagctttct    2580
aatatgattg taaagtcttg caaatgcagc taaaattctt ggaaaagtgg caagaccaaa    2640
atgacaatga tgatgataat gatgatgacg acgacaacga tgatgcttgt aacaagaaaa    2700
cataagagag ccttggttca tcagtgttaa aaaattttg aaaaggcggt actagttcag     2760
acactttgga agtttgtgtt ctgtttgtta aaactggcat ctgacacaaa aaaagttgaa    2820
ggccttattc tacatttcac ctactttgta agtgagagag acaagaagca aattttttt    2880 aaagaaaaaa ataaacactg gaagaattta ttagtgttaa ttatgtgaac aacgacaaca    2940
acaacaacaa caacaaacag gaaaatccca ttaagtggga ttgctgtacg taccgttcct    3000
atcccgcgcc tcacttgatt tttctgtatt gctatgcaat aggcacccct cccattctta    3060
ctcttagagt taacagtgag ttattttattg tgtgttacta taatgaac gtttcattgc     3120 ccttggaaaa taaacaggt gtataaagtg gagaccaaat actttgccag aaactcatgg    3180
atggcttaag gaacttgaac tcaaacgagc cagaaaaaaa gaggtcatat taatgggatg    3240
aaaacccaag tgagttatta tatgaccgag aaagtctgca ttaagataaa gaccctgaaa    3300
acacatgtta tgtatcagct gcctaaggaa gcttcttgta aggtccaaaa actaaaaaga    3360
ctgttaataa aagaaacttt cagtcagaat aagtctgtaa gttttttttt ttcttttta    3420 ttgtaaatgg ttcttttgtca gtttagtaaa ccagtgaaat gttgaaatgt tttgacatgt    3480
actggtcaaa cttcagacct taaaatattg ctgtatagct atgctatagg ttttttcctt    3540
tgttttggta tatgtaacca tacctatatt attaaaatag atggatatag aagccagcat    3600
aattgaaaac acatctgcag atctcttttg caaactatta aatcaaaaca ttaactactt    3660
tatgtgtaat gtgtaaattt ttaccatatt ttttatattc tgtaataatg tcaactatga    3720
tttagattga cttaaatttg ggctctttt aatgatcact cacaaatgta tgtttctttt     3780
agctggccag tacttttgag taaagcccct atagttgac ttgcactaca aatgcatttt     3840
ttttttaata catttgccc tacttgtgct ttgtgtttct ttcattatta tgacataagc     3900
tacctgggtc cacttgtctt ttcttttttt tgtttcacag aaaagatggg ttcgagttca    3960
gtggtcttca tcttccaagc atcattacta accaagtcag acgttaacaa attttttatgt    4020 taggaaaagg aggaatgtta tagatacata gaaaattgaa gtaaaatgtt tcatttttag    4080
caaggattta gggttctaac taaaactcag aatctttatt gagttaagaa aagtttctct    4140
accttggttt aatcaatatt tttgtaaaat cctattgtta ttacaaagag gacacttcat    4200
aggaaacatc tttttcttta gtcaggtttt taatattcag ggggaaattg aaagatatat    4260
attttagtcg atttttcaaa aggggaaaaa agtccaggtc agcataagtc attttgtgta    4320
tttcactgaa gttataaggt ttttataaat gttcttgaa ggggaaaagg cacaagccaa     4380
tttttcctat gatcaaaaaa ttctttcttt cctctgagtg agagttatct atatctgagg    4440
ctaaagttta ccttgcttta ataataatt tgccacatca ttgcagaaga ggtatcctca     4500
tgctggggtt aatagaatat gtcagtttat cacttgtcgc ttatttagct ttaaaataaa    4560
aattaatagg caaagcaatg gaatatttgc agtttcacct aaagagcagc ataaggaggc    4620
```

-continued

```
gggaatccaa agtgaagttg tttgatatgg tctacttctt ttttggaatt tcctgaccat    4680
taattaaaga attggatttg caagtttgaa aactggaaaa gcaagagatg ggatgccata    4740
atagtaaaca gcccttgtgt tggatgtaac ccaatcccag atttgagtgt gtgttgatta    4800
ttttttttgtc ttccactttt ctattatgtg taaatcactt ttatttctgc agacatttc    4860
ctctcagata ggatgacatt ttgttttgta ttattttgtc tttcctcatg aatgcactga    4920
taatatttta aatgctctat tttaagatct cttgaatctg tttttttttt ttttaatttg    4980
ggggttctgt aaggtcttta tttcccataa gtaaatattg ccatgggagg ggggtggagg    5040
tggcaaggaa ggggtgaagt gctagtatgc aagtgggcag caattatttt tgtgttaatc    5100
agcagtacaa tttgatcgtt ggcatggtta aaaaatggaa tataagatta gctgttttgt    5160
attttgatga ccaattacgc tgtattttaa cacgatgtat gtctgttttt gtggtgctct    5220
agtggtaaat aaattatttc gatgatatgt ggatgtcttt ttcctatcag taccatcatc    5280
gagtctagaa acacctgtg atgcaataag actatctcaa gctggaaaag tcataccacc     5340
tttccgattg ccctctgtgc tttctcctt aaggacagtc acttcagaag tcatgcttta    5400
aagcacaaga gtcaggccat atccatcaag gatagaagaa atccctgtgc cgtcttttta    5460
ttcccttatt tattgctatt tggtaattgt ttgagattta gtttccatcc agcttgactg    5520
ccgaccagaa aaaatgcaga gagatgtttg caccatgctt tggctttctg gttctatgtt    5580
ctgccaacgc cagggccaaa agaactggtc tagacagtat cccctgtagc cccataactt    5640
ggatagttgc tgagccagcc agatataaca agagccacgt gctttctggg gttggttgtt    5700
tgggatcagc tacttgcctg tcagtttcac tggtaccact gcaccacaaa caaaaaaacc    5760
caccctatt cctccaattt ttttggctgc tacctacaag accagactcc tcaaacgagt    5820
tgccaatctc ttaataaata ggattaataa aaaagtaat tgtgactcaa aaaaaaaaaa    5880
aa                                                                   5882

<210> SEQ ID NO 2
<211> LENGTH: 17
<212> TYPE: DNA
<213> ORGANISM: Artificial Sequence
<220> FEATURE:
<223> OTHER INFORMATION: modified TGF-beta2 oligonucleotide

<400> SEQUENCE: 2 caaagtatt ggtctcc                                                    17

<210> SEQ ID NO 3
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 3
agtatttggt ctcc                                                      14

<210> SEQ ID NO 4
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 4
aagtatttgg tctc                                                      14
```

```
<210> SEQ ID NO 5
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 5
aagtatttgg tctcc                                                      15

<210> SEQ ID NO 6
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 6
agtatttggc tctc                                                       14

<210> SEQ ID NO 7
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 7
agtatttggt ctcca                                                      15

<210> SEQ ID NO 8
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 8
aagtatttgg tctcc                                                      15

<210> SEQ ID NO 9
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 9
caaagtattt ggtctc                                                     16

<210> SEQ ID NO 10
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 10
caaagtattt ggtct                                                      15

<210> SEQ ID NO 11
<211> LENGTH: 14
<212> TYPE: DNA
<213> ORGANISM: Artificial Sequence
<220> FEATURE:
```

```
<223> OTHER INFORMATION: modified TGF-beta2 oligonucleotide

<400> SEQUENCE: 11
caaagtattt ggtc                                                        14

<210> SEQ ID NO 12
<211> LENGTH: 16
<212> TYPE: DNA
<213> ORGANISM: Artificial Sequence
<220> FEATURE:
<223> OTHER INFORMATION: modified TGF-beta2 oligonucleotide

<400> SEQUENCE: 12
aaagtatttg gtctcc                                                      16

<210> SEQ ID NO 13
<211> LENGTH: 15
<212> TYPE: DNA
<213> ORGANISM: Artificial Sequence
<220> FEATURE:
<223> OTHER INFORMATION: modified TGF-beta2 oligonucleotide

<400> SEQUENCE: 13
aaagtatttg gtctc                                                       15

<210> SEQ ID NO 14
<211> LENGTH: 14
<212> TYPE: DNA
<213> ORGANISM: Artificial Sequence
<220> FEATURE:
<223> OTHER INFORMATION: modified TGF-beta2 oligonucleotide

<400> SEQUENCE: 14
aaagtatttg gtct                                                        14

<210> SEQ ID NO 15
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 15
aaagtatttg gtc                                                         13

<210> SEQ ID NO 16
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 16
aagtatttgg tct                                                         13

<210> SEQ ID NO 17
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 17
aagtatttgg tc                                                          12
```

```
<210> SEQ ID NO 18
<211> LENGTH: 13
<212> TYPE: DNA
<213> ORGANISM: Artificial Sequence
<220> FEATURE:
<223> OTHER INFORMATION: modified TGF-beta2 oligonucleotide

<400> SEQUENCE: 18
agtatttggt ctc                                                          13

<210> SEQ ID NO 19
<211> LENGTH: 12
<212> TYPE: DNA
<213> ORGANISM: Artificial Sequence
<220> FEATURE:
<223> OTHER INFORMATION: modified TGF-beta2 oligonucleotide

<400> SEQUENCE: 19
agtatttggt ct                                                           12

<210> SEQ ID NO 20
<211> LENGTH: 11
<212> TYPE: DNA
<213> ORGANISM: Artificial Sequence
<220> FEATURE:
<223> OTHER INFORMATION: modified TGF-beta2 oligonucleotide

<400> SEQUENCE: 20
agtatttggt c                                                            11
```